United States Patent [19]
Gall

[11] 3,992,393
[45] Nov. 16, 1976

[54] NOVEL IMIDAZOBENZODIAZEPINE DERIVATIVE

[75] Inventor: Martin Gall, Kalamazoo, Mich.

[73] Assignee: The Upjohn Company, Kalamazoo, Mich.

[22] Filed: Oct. 20, 1975

[21] Appl. No.: 623,970

[52] U.S. Cl. .............................. 260/296 T; 424/263
[51] Int. Cl.² ........................................ C07D 487/04
[58] Field of Search ................................. 260/296 T

[56] References Cited
UNITED STATES PATENTS

| | | | |
|---|---|---|---|
| 3,910,946 | 10/1975 | Gall | 260/309 |
| 3,927,016 | 12/1975 | Hester | 260/309 |

Primary Examiner—John D. Randolph
Attorney, Agent, or Firm—Hans L. Berneis

[57] ABSTRACT

8-Bromo-1-[(dimethylamino)methyl]-6-(2-pyridyl)-4H-imidazo[1,2-a][1,4]benzodiazepine of the formula:

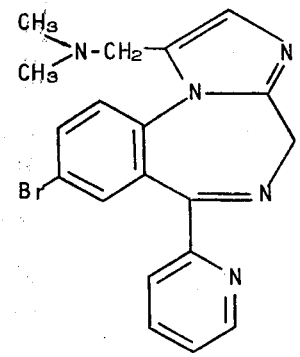

is prepared, which compound has anti-depressant, anti-convulsant, and anti-anxiety activities and is particularly useful in mammals to combat depression and anxieties.

1 Claim, No Drawings

NOVEL IMIDAZOBENZODIAZEPINE DERIVATIVE

BACKGROUND OF THE INVENTION

1. Field of the Invention

This invention is directed to a new organic compound and is particularly concerned with 8-bromo-1-[(dimethylamino)methyl]-6-(2-pyridyl)-4H-s-imidazo[1,2-a][1,4]-benzodiazepine and a process of production thereof.

The new compound of this invention has antidepressant activity which is surprising in view of the fact that the known 6-phenyl analogues, 1-aminomethyl-6-phenyl-4H-imidazo[1,2-a][1,4]benzodiazepines are essentially tranquilizers [U.S. Pat. No. 3,910,946]. For examples a comparison of 8-chloro-1-[(dimethylamino)-methyl]-6-phenyl-4H-imidazo[1,2-a][1,4]benzodiazepine (A) with the compound of this invention, 8-bromo-1-[(dimethylamino)methyl]-6-(2-pyridyl)-4H-imidazo[1,2-a][1,4]benzodiazepine (B) illustrates the anti-depressant activity of B:

|   | Oxotremorine Hypothermia Antagonism mg./kg. | Apomorphine Gnawing Potentiation mg./kg. | Yohimbine Aggregatic Toxicity mg./kg. |
|---|---|---|---|
| A | 42 mg./kg. | >50 mg. | >50 |
| B | 1.1 | 29.7 | 21 |

Differences between the two compounds also exist concerning the anticonvulsant activity (metrazol protection) and anti-anxiety activity. Compound A requires 12.5 mg./kg. to protect the animal (mouse) from metrazol-caused convulsions; compound B required only 3.7 mg./kg. The Hypoxic Stress (anxiety) is not counteracted by compound A unless dosages of more than 50 mg./kg. produce such a result, whereas compound B provides protection at 35.4 mg./kg. (The tests are described herein below).

The novel compound of this invention and the process of production thereof can be illustratively shown by the following scheme:

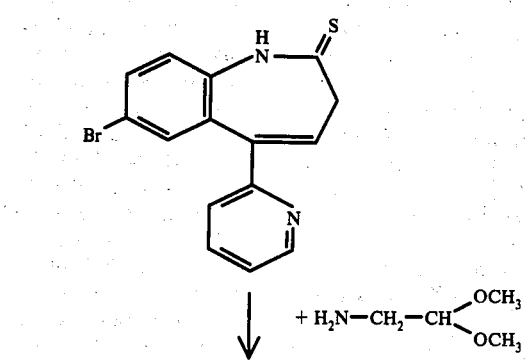

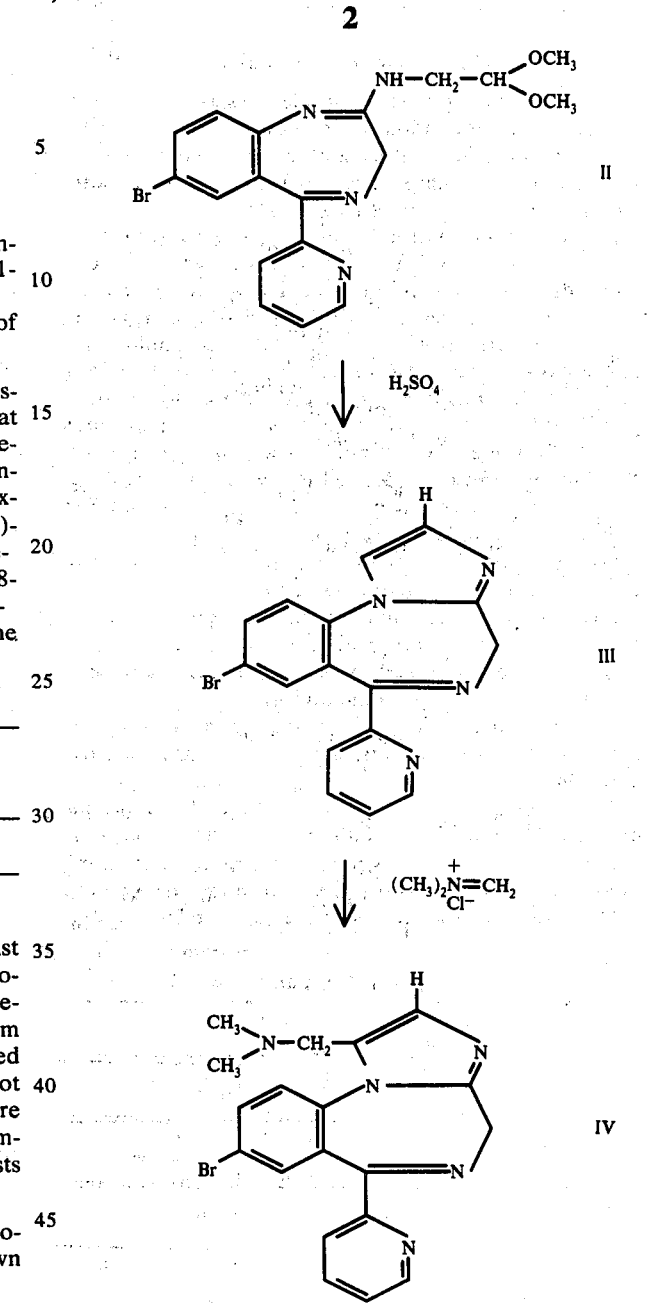

DETAILED DESCRIPTION OF THE PREFERRED EMBODIMENT

Compound IV is particularly intended to be used as an anti-depressant and anti-anxiety compound in mammals, including man. The mammals this drug is intended for include particularly barnyard animals, cows, goats, sheep, swine, during transportation by rail or truck. Also dogs and cats, as well as zoo animals, which are mammals, can be treated with this compound. Form 1 to 15 mg./kg. dosages in small mammals (under 10 kg.) should be applied, while in larger mammals 0.3 to 10 mg./kg. should be sufficient to overcome depressions and/or anxieties.

The anti-depressant action:

The main function of an antidepressant is to return the depressed individual up to normal function. This should be carefully differentiated from psychic stimulants such as the amphetamines which produce overstimulation in the normal individual.

Many different methods have been and are used to evaluate anti-depressant activity. In general these methods involve antagonism of a depressant such as reserpine or tetrabenazine or a synergistic increase of the toxicity of certain compounds (i.e. yohimbine or 3,4-dihydroxyphenalanine) and comparison of the drug action of the new compound with other known antidepressants. No single test alone can determine whether or not a new compound is an antidepressant or not, but the profile evidenced by various tests will establish the anti-depressant action if present. A number of such tests are described below.

Hypothermic tests with oxotremorine, 1-[4-(pyrrolidinyl)-2-butynyl]-2-pyrrolidinone:

Oxotremorine (as well as apomorphine and tetrabenazine) produces hypothermic responses in mice. This response is blocked by anticholinergics and antidepressants such as atropine and imipramine.

Oxotremorine produces a very pronounced hypothermia which reaches a peak 60 minutes after administration.

At 0.6 mg./kg. the body temperature of a mouse is decreased about 13° F. (when the mouse is kept at room temperature). This temperature decrease is antagonized by anti-depressants e.g. desipramine, imipramine, doxepine, and others as can be seen from Table I.

TABLE I

Effect of Various Compounds on Oxotremorine-Induced Hypothermia in Mice

| | Dose mg./kg., I.P. | Absorption Time (min) | Body Temperature °F.- Change From Vehicle Control After Minutes | | | |
|---|---|---|---|---|---|---|
| | | | 15 | 30 | 60 | 90 |
| Oxotremorine (Control) | 0.6 | | −5.8 | 11.6 | −13.2 | −8.0 |
| Desipramine | 25 | 30 | −3.5 | −3.5 | −4.1 | −3.6 |
| Imipramine | 23 | 30 | −0.4 | −3.3 | −5.6 | −6.4 |
| Iprindole | 25 | 30 | −6.3 | −11.8 | −12.8 | −11.9 |
| Doxepine | 25 | 30 | −2.3 | −7.1 | −11.0 | −12.3 |
| Amitriptyline | 25 | 30 | +0.7 | −2.4 | −5.4 | −6.8 |
| Amphetamine | 5 | 30 | −1.5 | −4.3 | −4.4 | −2.2 |

The compound of formula IV was tested as follows:

Four male mice of 18–22 g. (Strain CF=Carworth Farms) were injected intraperitoneally with 1 mg. of oxotremorine. The lowering of the body temperature was measured rectally with an electronic thermometer, before and 30 minutes after drug administration. After the drug administration the mice were kept at 19° C. in cages. A rise of 4° Fahrenheit over the oxotremorine body temperature was taken as indicative of antidepressant activity. A dosage of 1.1 mg./kg. of the test compound produced the desired result.

Potentiation of yohimbine aggregation toxicity: the $LD_{50}$ of yohimbine hydrochloride [YCl] in mice is 45 mg./kg. i.p. Administration of 30 mg./kg. of [YCl] was non-lethal. If an anti-depressant is administered prior to the [YCl] (30 mg./kg.). The lethality of the [YCl] is increased.

As a control ten male CF mice, 18–22 g., are injected with [YCl] (30 mg./kg.) in saline solution. Groups of ten mice are injected with varying doses of the antidepressant 30 minutes before the administration of [YCl] (30 mg./kg.). After two hours the $LD_{50}$'s are determined. No mice or only one mouse is killed from 30 mg./kg. of [YCl]. In the presence of an anti-depressant an increase in the toxicity of [YCl] is found. The $ED_{50}$ value of the test compound IV in causing 50% of the mice to die is 29.7 mg./kg.

Potentiation of apomorphine gnawing: a group of 4 mice (male, CF, 18–22 g.) are administered the test compound intraperitoneally one hour prior to the subcutaneous injection of apomorphine hydrochloride 1 mg./kg. The mice are then placed in a plastic box [6 inch × 11 inch × 5 inch] lined in the bottom with a cellophane-backed, absorbent paper. The degree of damage to the paper at the end of 30 minutes is scored from zero to 4. The scores 3 and 4 indicated that the compound is a potentiator of apomorphine in this test. The test compound IV gave a positive test at 21 mg./kg.

The same testing system was used for 8-chloro-1-[2-(dimethylamino)methyl]-6-phenyl-4H-s-imidazo[4,3-a][1,4]-benzodiazepine (A) with the results stated before.

Antagonism of pentylenetetrazol (Metrazol) - Induced Tonic Seizures

In this procedure, a group of 4 CF-1 male mice (18–22 g. each) is injected intraperitoneally with the test compound prepared in 0.25% methylcellulose. After 30 minutes, pentylenetetrazole is injected s.c. at 85 mg./kg. Fifteen minutes after the pentylenetetrazol, a set of keys is rattled over the cage. A compound is considered active at a dosage where two or more animals in the group are protected from tonic extensor seizures. This test is useful for detecting anticonvulsant activity. Compound IV was found to be active at 3.7 mg./kg.

Prolongation of Hypoxic Survival

Pretreatment of mice exposed to the stress of progressive hypoxia and hypercapnia with anxiolytics results in a prolongation of survival. This effect appears to be relatively specific. Chronic treatment with chlordiazepoxide HCl (Librium) leads to tolerance development to the anticonvulsant and gamma-butyrolactone potentiating effects of this compound, but not to its hypoxic survival prolonging effects. Since tolerance does not appear to develop to the clinical anxiolytic effects of benzodiapines, the hypoxic survival test can be a useful screening technique for anxiolytic drugs.

Male $CF_2$ mice (26–28 g.) were used in these studies. Thirty minutes after intraperitoneal pretreatment (test agent suspended in 0.25% methylcellulose or vehicle alone, 1 cc/100 g. body weight) the mice were placed singly in 125 ml. Erlenmeyer flasks. The receptacles were tightly stoppered and the survival time (time from stoppering to the last respiratory effort) of each animal noted. Each compound was tested at three or more doses spaced at 0.3 log intervals. Six mice were used per dose with six vehicle injected controls run simultaneously. The mean (15–18 minutes) and standard deviation (1–2 minutes) of the survival time for the vehicle treated mice were used to convert the data to a quantal form in the following manner. All survival times that differed from the mean of the controls by more than 2 standard deviations were scored as a drug effect. $ED_{50}$'s were calculated by the method of Spearman and Karber (Finney, D. J., Statistical Method in Biological Assay, Hafner Publ., Co., N.Y., 1952).

Compound IV activity protected the mice at a dosage of 35.4 mg./kg.

The pharmaceutical forms of compound IV including any pharmacologically acceptable acid addition salts of IV, include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, constarch, stearic acid, methylcellulose and the like may be used as carriers or for coating purposes. Water and oils, e.g. coconut oil, sesame oil, safflower oil, cottonseed oil, peanut oil may be used for preparing solutions or suspensions of the active drug. Sweetening, coloring and flavoring agents may be added.

For mammals and birds food premixes, with starch, oatmeal, dried fishmeat, fishmeal, flour, and the like can be prepared.

The following Examples are illustrative of the compound and process of the present invention, but are not to be construed as limiting.

EXAMPLE 1

[[7-Bromo-5-(2-pyridyl)-3H-1,4-benzodiazepine-2-yl]amino]acetaldehyde, dimethyl-acetal A suspension of 15 g. (45 mmol) of 7-bromo-1,3-dihydro-5-(2-pyridyl)-2H-1,4-benzodiazepine-2-thione and 12 g. (114 mmol) of aminoacetaldehyde dimethyl acetal (Aldrich) in 500 ml. of n-butanol is heated to reflux for 4 hours with a stream of nitrogen bubbling through the reaction. (Within 1 hour all solids have dissolved). The solvent is removed in vacuo and the residue taken up in chloroform. The chloroform solution is washed with water and brine, dried over sodium sulfate and concentrated to a yellow brown oil in vacuo. On trituration with ethyl acetate this affords 16.5 g. (91%) of [[7-bromo-5-(2-pyridyl)-3H-1,4-benzodiazepine-2-yl]amino]- acetaldehyde, dimethyl-acetal. The analytical sample, recrystallized from ethyl acetate/hexane mixtures, has a melting point 155°–157° C.

Anal. calcd. for $C_{18}H_{19}BrN_4O_2$: C, 53.61; H, 4.75; N, 13.90; Br, 19.81.

Found: C, 53.61; H, 4.70; N, 13.75; Br, 19.83.

EXAMPLE 2

8-Bromo-6-(2-pyridyl)-4H-imidazo[1,2-a][1,4]benzodiazepine

A solution of 15 g. (37 mmol) of [[7-bromo-5-(2-pyridyl)-3H-1,4-benzodiazepine-2-yl]amino]acetaldehyde dimethyl-acetal in 50 ml. of concentrated sulfuric acid is allowed to stir at room temperature under nitrogen overnight, poured onto crushed ice and neutralized with an aqueous sodium hydroxide solution. The product is extracted with chloroform and the chloroform washed with brine, dried over sodium sulfate and concentrated to an oil in vacuo. On trituration, 10.2 g. (81%) of 8-bromo-6-(2-pyridyl)-4H-imidazo[1,2-a][1,4] benzodiazepine, a yellow crystalline product of melting point 208°–210°, is obtained.

Anal. calcd. for $C_{16}H_{11}BrN_4$: C, 56.65; H, 3.27; N, 16.56; Br, 23.56.

Found: C, 56.34; H, 3.22; N, 16.47; Br, 23,54.

EXAMPLE 3

1-(Dimethylamino)methyl-8-bromo-6-(2-pyridyl)-4H-imidazo[1,2-a][1,4]benzodiazepine A solution of 0.51 g. (5.0 mmol) of $[(CH_3)_2N]_2CH_2$ in 10 ml. of dimethylformamide is cooled to 0° C. and stirred for 10 minutes. To this solution, 0.355 ml. (0.39 g., 5.0 mmol) of acetyl chloride is added dropwise over a period of 15 minutes under nitrogen atmosphere to afford the Mannich salt $Cl^-CH_2=^+NMe_2$ as a white precipitate.

To a suspension of the Mannich base above in 10 ml. of dimethylformamide is added 1.0 g. (3.00 mmol) of 8-bromo-6-(2-pyridyl)-4H-imidazo[1,2-a][1,4]benzodiazepine. The mixture is heated on a steam bath for a total of 2 hours, then quenched in cold water, neutralized with a 10% aqueous sodium hydroxide solution and extracted with chloroform. The chloroform layer is washed with water and brine, dried over anhydrous sodium sulfate and concentrated in vacuo to an oil, which is chromatographed over 100 g. of silica gel by eluting with 3% methanol/97% chloroform mixtures. The product is collected and crystallized from ethyl acetate to afford 150 mg. of 1-(dimethylamino)methyl-8-bromo-6-(2-pyridyl)-4H-imidazo[1,2-a][1,4]benzodiazepine as a tan solid of melting point 200°–202° C.

Anal. calcd. for $C_{19}H_{18}BrN_5$, mw 396.28: C, 57.58; H, 4.58; N, 17.68; Br, 20.16.

Found: C, 57.50; H, 4.32; N, 17.26; Br, 20.63.

I claim:

1. 8-Bromo-1-[(dimethylamino)methyl]-6-(2-pyridyl)4H-imidazo[1,2-a][1,4] benzodiazepine of the formula:

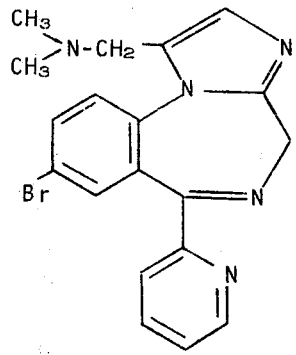

* * * * *